United States Patent
Schaub et al.

(10) Patent No.: US 12,172,958 B2
(45) Date of Patent: Dec. 24, 2024

(54) SYNTHESIS OF N-VINYL COMPOUNDS BY REACTING NH-COMPOUNDS WITH ACETYLENE IN PRESENCE OF HOMOGENEOUS PHOSPHINE CATALYST

(71) Applicant: BASF SE, Ludwigshafen Am Rhein (DE)

(72) Inventors: Thomas Schaub, Ludwigshafen (DE); Pavel Tuzina, Ludwigshafen (DE); Frank Bienewald, Ludwigshafen (DE); Maximilian Menche, Ludwigshafen (DE); Nikolai Amadeus Sitte, Heidelberg (DE); A. Stephen K. Hashmi, Heidelberg (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 18/561,835

(22) PCT Filed: May 10, 2022

(86) PCT No.: PCT/EP2022/062554
§ 371 (c)(1),
(2) Date: Nov. 17, 2023

(87) PCT Pub. No.: WO2022/243097
PCT Pub. Date: Nov. 24, 2022

(65) Prior Publication Data
US 2024/0270690 A1 Aug. 15, 2024

(30) Foreign Application Priority Data
May 19, 2021 (EP) .................................... 21174651

(51) Int. Cl.
*C07D 207/267* (2006.01)
*C07D 263/20* (2006.01)

(52) U.S. Cl.
CPC ....... *C07D 207/267* (2013.01); *C07D 263/20* (2013.01)

(58) Field of Classification Search
CPC .......................... C07D 207/267; C07D 263/20
See application file for complete search history.

(56) References Cited

FOREIGN PATENT DOCUMENTS

| EP | 0512656 A2 | 11/1992 |
|---|---|---|
| EP | 0646571 A1 | 4/1995 |
| WO | 2021/122249 | 6/2021 |

OTHER PUBLICATIONS

International Search Report received for PCT Application No. PCT/EP2022/062554, mailed on Aug. 23, 2022, 4 pages.
International Preliminary Report on Patentability received for PCT Application No. PCT/EP2022/062554, mailed on Aug. 9, 2023, 11 pages.
Miossec et al., "Inter- or Intramolecular Coupling of β-Haloamino Acids with Alkynes", Synthesis, Nov. 1994, pp. 1171-1174.
Semina et al., "Ruthenium-Catalyzed Synthesis of Vinylamides at Low Acetylene Pressure", Chem. Commun., vol. 56, 2020, pp. 5977-5980.
Sitte et al., "Phosphine-Catalyzed Vinylation at Low Acetylene Pressure", The Journal of Organic Chemistry, vol. 86, No. 18, 2021, pp. 13041-13055.
Trost et al., "Nucleophilic α-Addition to Alkynoates. A Synthesis of Dehydroamino Acids", J. Am. Chem. Soc., vol. 119, No. 32, 1997, pp. 7595-7596.
Written Opinion received for PCT Application No. PCT/EP2022/062554, mailed on Aug. 23, 2022, 6 pages.
Moran, et al., "Reactor Types and Their Industrial Applications", Ullmann's Encyclopedia of Industrial Chemistry, Chapter 3.3, Reactors for Gas-Liquid Reaction, Nov. 2016, pp. 1-49.
Trotus, et al., "Catalytic Reactions of Acetylene: A Feedstock for the Chemical Industry Revisited", Chemical Reviews, vol. 114, Issue 3, Feb. 12, 2014, pp. 1761-1782.
Walter Reppe, "Vinylierung", Justus Liebigs Annalen Der Chemie, vol. 601, Issue 1, Jul. 28, 1956, pp. 81-138.

*Primary Examiner* — Kamal A Saeed
(74) *Attorney, Agent, or Firm* — Grüneberg and Myers PLLC

(57) ABSTRACT

A process to produce N-vinyl compounds by homogeneous catalysis can be performed. Acetylene is reacted with a compound having at least one nitrogen bearing a substitutable hydrogen residue in a liquid phase in the presence of at least one phosphine as a catalyst to produce the compounds.

7 Claims, No Drawings

SYNTHESIS OF N-VINYL COMPOUNDS BY REACTING NH-COMPOUNDS WITH ACETYLENE IN PRESENCE OF HOMOGENEOUS PHOSPHINE CATALYST

CROSS-REFERENCE TO RELATED APPLICATIONS

This application is a National Stage entry under § 371 of International Application No. PCT/EP2022/062554, filed on May 10, 2022, and which claims the benefit of priority to European Patent Application No. 21174651.6, filed on May 19, 2021. The content of each of these applications is hereby incorporated by reference in its entirety.

Object of the invention is a process to produce N-vinyl compounds by homogeneous catalysis, wherein acetylene is reacted with a compound comprising a hydrogen substituted nitrogen in the liquid phase in the presence of a phosphine as catalyst.

In the classical and industrially carried out vinylation of N—H compounds with acetylene, usually strong alkaline bases were used as the catalyst (see: Chemical Reviews, 2014, 114, 1761-1782 and Liebigs Annalen der Chemie, 1956, 601, 81-138). Frequently the alkaline base catalyst needs to be prepared in a separate process step just before the reaction ("base preparation"). A drawback of this state-of-the-art approach are the harsh and strongly basic conditions, which are leading to reduced yields especially when base-sensitive substrates like cyclic carbamates or lactams are used to produce the corresponding N-vinyl compounds.

To overcome these intrinsic drawbacks and run the vinylation under milder conditions, different approaches were reported, to use more efficient catalysts which can facilitate the N-vinylation with acetylene under milder conditions.

From EP 512 656 it is known to produce vinyl compounds by reacting acetylene with a Brønsted acid in presence of a heterogeneous, supported catalyst comprising ruthenium.

EP-A 646571 discloses a homogeneously catalyzed reaction of acetylene with ammonia or a primary or secondary amino compound at 1 to 30 bars; 20 bars are used in the examples. Various catalysts are disclosed, inter alia catalysts based on ruthenium are mentioned.

Chemical Communications, 2020, 56, 5977-5980 discloses homogeneously catalyzed N-vinylation of cyclic amides and related cyclic compounds using a Ruthenium catalyst with phosphine ligands under low acetylene pressures of 1.5 bar.

A drawback of the afore mentioned systems is the use of the expensive precious metal Ruthenium as the active catalyst. To overcome this drawback, precious metal-free catalyst systems working under mild reaction conditions (e.g. less basic or acidic) would be beneficial.

Journal of the American Chemical Society, 1997, 119, 7595-7596 describes the use of phosphines as catalysts in the addition of internal and external alkynoates to activated NH-compounds as phthalimides and sulfonamides to the corresponding N-vinyl-compounds using phosphines as catalysts. A drawback of this system is, that large amounts (more than 50 mol %) of acidic co-catalysts as Acetic Acid or phenol are required. Also, it could not be shown, that this catalytic system works for the vinylation of less acidic NH-compounds with simple acetylene as the alkyne.

As acetylene is gaseous, reactions with acetylene are usually performed under pressure. It is desirable from the economical as well as reaction safety point of view to keep the pressure as low as possible.

It was an object of this invention to provide a process for the synthesis of N-vinyl compounds, which can be performed at low pressure, under less basic or acidic conditions and without the need for base preparation as described in the state-of-the-art and wherein the N-vinyl compounds are obtained in high yield and selectivity.

Accordingly, the process above has been found.

To the N—H Compound

The N—H-compound is an organic nitrogen containing compound with at least one nitrogen bearing a substitutable hydrogen residue with a $pK_a$ deterimned in Dimethylsulfoxide of this hydrogen in the range of 14 to 28. The experimental $pK_a$-values were adapted from literature and measured by the spectrophotometric method in DMSO against indicator at 25° C., see: J. Am. Chem. Soc. 1975, 97, 7006-7014 and J. Org. Chem. 1980, 46, 3295-3299. The corresponding experimental $pK_a$ values were taken from the following references: F. G. Bordwell, H. E. Fried, J. Org. Chem. 1991, 56, 4218-4223; B. Valter, M. I. Terekhova, E. S. Petrov, J. Stehliček, J. Šebenda, Collect. Czech. Chem. Commun. 1985, 50, 834-839; F. G. Bordwell, Acc. Chem. Res. 1988, 21, 456-463; F. G. Bordwell, G. E. Drucker, H. E. Fried, J. Org. Chem. 1981, 46, 632-635. For the substrates, where the $pK_a$ values where not experimentally available, the corresponding $pK_a$ values in DMSO were calculated via DFT calculations according the following method:

All geometry optimizations were carried out at the BP86/def2-SV(P)[1] level of theory. Stationary points were verified via analysis of the vibrational frequencies at the level of geometry optimization. Final electronic energies were obtained by single-point calculations at the PBE0-D3(BJ)/def2-QZVPP[2] level of theory employing Grimme's D3 dispersion correction[3] incorporating Becke-Johnson damping.[4] All quantum-chemical calculations were carried out using the TURBOMOLE program[5] (Version 7.3) with the resolution-of-identity (RI) approximation[6] and the corresponding auxiliary basis sets[7] implemented in the program. Zero-point vibrational energies and thermodynamic corrections were obtained at the level of geometry optimization (T=298.15 K and p=1 bar). Solvent corrections to Gibbs free energies in DMF were calculated for all species with the conductor-like screen model for real solvents (COSMO-RS)[8] carried out with the COSMOtherm program[9] (Version 18.0.0; Revision 4360). All pKas were calculated using a proton exchange scheme with referencing to either 2-Pyrrolidone or 2-Oxazolidinone, which have been extensively used before e.g. by Ho et al.[10]

$$\Delta G_{proton\ exchange} = \Delta G_{HRef} + \Delta G_{A^-} - \Delta G_{Ref^-} - \Delta G_{HA} pK_a(HA) =$$

$$\frac{\Delta G_{proton\ exchange}}{RT\ln(10)} + pK_a^{exp}(HRef)$$

References for the $pK_a$-calculations: [1] (a) Perdew, J. P., Density-functional approximation for the correlation energy of the inhomogeneous electron gas. Phys. Rev. B 1986, 33, 8822-8824; (b) Becke, A. D., Density-functional exchange-energy approximation with correct asymptotic behavior. Phys. Rev. A 1988, 38, 3098-3100; (c) Weigend, F.; Ahlrichs, R., Balanced basis sets of split valence, triple zeta valence and quadruple zeta valence quality for H to Rn: Design and assessment of accuracy. Phys. Chem. Chem. Phys. 2005, 7, 3297-3305. [2] Ernzerhof, M.; Scuseria, G. E., Assessment of the Perdew-Burke-Ernzerhof exchange-correlation functional. J. Chem. Phys. 1999, 110, 5029-5036; (b) Weigend, F.; Furche, F.; Ahlrichs, R., Gaussian basis sets of quadruple zeta valence quality for atoms H—Kr. *J. Chem. Phys.* 2003, 119, 12753-12762; (c) Weigend, F.; Ahlrichs, R., Balanced basis sets of split valence, triple zeta valence and quadruple zeta valence quality for H to Rn: Design and assessment of accuracy. *Phys. Chem. Chem. Phys.* 2005, 7, 3297-3305. [3] Grimme, S.; Antony, J.; Ehrlich, S.; Krieg, H., A consistent and accurate ab initio parametrization of density functional dispersion correction (DFT-D) for the 94 elements H—Pu. *J. Chem. Phys.* 2010, 132, 154104-154119. [4] Grimme, S.; Ehrlich, S.; Goerigk, L., Effect of the damping function in dispersion corrected density functional theory. *J. Comput. Chem.* 2011, 32, 1456-1465. [5] (a) Ahlrichs, R.; Bär, M.; Häser, M.; Horn, H.; Kölmel, C., Electronic structure calculations on workstation computers: The program system turbomole. *Chem. Phys. Lett.* 1989, 162, 165-169; (b) *TURBOMOLE V7.3 2018, a development of University of Karlsruhe and Forschungszentrum Karlsruhe GmbH*, TURBOMOLE GmbH, available from http://www.turbomole.com; (c) Treutler, O.; Ahlrichs, R., Efficient molecular numerical integration schemes. *J. Chem. Phys.* 1995, 102, 346-354. [6] (a) Weigend, F., Accurate Coulomb-fitting basis sets for H to Rn. *Phys. Chem. Chem. Phys.* 2006, 8, 1057-1065; (b) Vahtras, O.; Almlöf, J.; Feyereisen, M. W., Integral approximations for LCAO-SCF calculations. *Chem. Phys. Lett.* 1993, 213, 514-518; (c) Eichkorn, K.; Treutler, O.; Öhm, H.; Haser, M.; Ahlrichs, R., Auxiliary basis sets to approximate Coulomb potentials. *Chem. Phys. Lett.* 1995, 240, 283-290; (d) Deglmann, P.; May, K.; Furche, F.; Ahlrichs, R., Nuclear second analytical derivative calculations using auxiliary basis set expansions. *Chem. Phys. Lett.* 2004, 384, 103-107. [7](a) Weigend, F.; Häser, M.; Patzelt, H.; Ahlrichs, R., RI-MP2: optimized auxiliary basis sets and demonstration of efficiency. *Chem. Phys. Lett.* 1998, 294, 143-152; (b) Hellweg, A.; Hättig, C.; Höfener, S.; Klopper, W., Optimized accurate auxiliary basis sets for RI-MP2 and RI-CC2 calculations for the atoms Rb to Rn. *Theor. Chem. Acc.* 2007, 117, 587-597. [8] (a) Klamt, A., Conductor-like Screening Model for Real Solvents: A New Approach to the Quantitative Calculation of Solvation Phenomena. *J. Phys. Chem.* 1995, 99, 2224-2235; (b) Klamt, A.; Jonas, V.; Burger, T.; Lohrenz, J. C. W., Refinement and Parametrization of COSMO-RS. *J. Phys. Chem. A* 1998, 102, 5074-5085. [9] (a) *COSMOtherm Version 18.0.0 (Revision 4360)*, COSMOlogic GmbH & Co KG, available from http://www.cosmologic.de; (b) Eckert, F.; Klamt, A., Fast solvent screening via quantum chemistry: COSMO-RS approach. *AIChE J.* 2002, 48, 369-385. [10] (a) Ho, J.; Ertem, M. Z., Calculating Free Energy Changes in Continuum Solvation Models. *J. Phys. Chem.* B 2016, 120, 1319-1329; (b) Ho, J.; Zwicker, V. E.; Yuen, K. K. Y.; Jolliffe, K. A., Quantum Chemical Prediction of Equilibrium Acidities of Ureas, Deltamides, Squaramides, and Croconamides. *J. Org. Chem.* 2017, 82, 10732-10736.

In a particularly preferred embodiment, the N—H-compound is a linear amide, a lactam, a cyclic carbamate, a pyrrole, an imidazole, a carbazole, an indol, a triazole, an urea or a diarylamine.

The linear amide comprises an amide group —NH—C(=O)—CR$_2$—.

The cyclic amide comprises an amide group —NH—C(=O)—CR$_2$— as element to the ring system.

The cyclic carbamate comprises a carbamate group —NH—C(=O)—O— as element to the ring system.

The imidazole comprises an imidazole unit with an NH-function.

The pyrrole comprises a pyrrole unit with an NH-function
The Diarylamine comprises a Ar$_2$NH function.
The Carbazole comprises a NH-function.
The Indol comprises a NH-function.
The Urea comprises a —NRH—C(=O)—NRH-function.
The pyrazole comprises a NH-function
The triazole comprises a NH-function The further carbon atoms of the linear or ring system, the imidazole or the aryl-groups of the diarylmine may be substituted or unsubstituted. Substituents to the carbon atoms may be, for example, carbonyl groups (=O), aliphatic or aromatic hydrocarbon groups that may comprise heteroatoms, notably oxygen in form of ether groups, two neighbored carbon atoms may be part of a further rings system, such as a cycloaliphatic or aromatic ring system.

Preferred linear amides are:
N-Methylacetamide (exp. pK$_a$=25.9)
Preferred cyclic amides are:
2-Pyrrolidone (exp. pK$_a$=24.2), 2-Piperidinone (exp. pK$_a$=26.6), Caprolactam (exp. pK$_a$=27.1), 8-Octanelactam (exp. pK$_a$=27.3), 2,3-Dihydro-1H-Isoindol-1-one (calc. pK$_a$=19.4), 2,5-Piperazinedione (calc. pK$_a$=20.9), 2-Thiazolidinone (calc. pK$_a$=18.6),
Preferred cyclic carbamate are:
2-Oxazolidinone (exp. pK$_a$=20.8), 4-Methyl-2-Oxazolidinone (calc. pK$_a$=18.4), 5-Methyl-2-Oxazolidinone (calc. pK$_a$=19.2), Tetrahydro-2H-1,3-Oxazin-2-one (calc. pK$_a$=22.4).
Preferred Pyrroles are:
Pyrrole (exp. pK$_a$=23), Indole (exp. pK$_a$=21.0)
Preferred Imidazoles are:
Imidazole (exp. pK$_a$=18.6), Benzimidalzole (exp. pK$_a$=16.4)
Preferred Pyrazoles are:
1H-Pyrazole (exp. pK$_a$=19.8)
Preferred Triazoles are:
1H-1,2,4-Triazole (exp. pK$_a$=14.8) and its derivatives
Preferred Diarylamines are:
Diphenylamine (exp. pK$_a$=25),
Preferred Carbazoles are:
Carbazole (exp. pK$_a$=19.9)
Preferred Ureas are:
Ethylenurea (calc. pK$_a$=24.4), Propyleneurea (calc. pK$_a$=26.2) and it's derivatives In the process of the invention, the NH-compound comprising a hydrogen substituted nitrogen is reacted with acetylene in the presence of at least one phosphine as catalyst; also called vinylation catalyst hereinafter.

To the Phosphine Catalyst

Suitable phosphines as catalyst for the vinylation of the process according to the invention are, for example, mono-, bi-, tri- and tetra dentate phosphines of the formulae I and II shown below, $$\begin{array}{c} R^1 \diagdown \diagup R^3 \\ P \\ | \\ R^2 \end{array} \quad (I)$$

$$\begin{array}{c} R^4 \diagdown \quad\quad\quad\quad\quad\quad \diagup R^6 \\ P-Y1-A-Y2-P \\ R^5 \diagup \quad | \quad \diagdown R^7 \\ Y3 \\ | \\ P \\ R^8 \diagup \diagdown R^9 \end{array}_n \quad (II)$$

where n is 0 or 1;

$R^1$ to $R^9$ are, independently of one another, unsubstituted or at least monosubstituted $C_1$-$C_{30}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

A is i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S, where the substituents are selected from the group consisting of:

$C_1$-$C_4$-alkyl, phenyl, F, Cl, Br, OH, $OR^{15}$, $NH_2$, $NHR^{15}$ or $N(R^{15})_2$, where $R^{15}$ is selected from $C_1$-$C_{10}$-alkyl and $C_5$-$C_{10}$-aryl; or ii) a bridging group of the formula (III) or (IV):

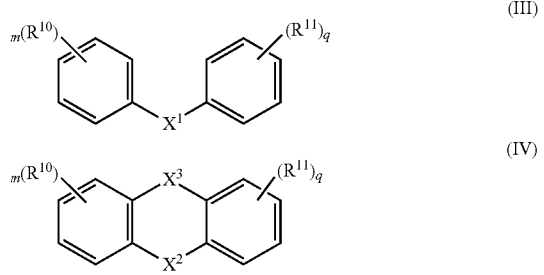

(III)

(IV)

m, q are, independently of one another, 0, 1, 2, 3 or 4;

$R^{10}$, $R^{11}$ are, independently of one another, selected from the group $C_1$-$C_{10}$-alkyl, F, Cl, Br, OH, $OR^{18}$, $NH_2$, $NHR^{18}$ and $N(R^{18})_2$, where $R^{18}$ is selected from $C_1$-$C_{10}$-alkyl and $C_5$-$C_{10}$-aryl;

$X^1$, $X^2$ are, independently of one another, NH, O or S;

$X^3$ is a bond, NH, $NR^{17}$, O, S or $CR^{18}R^{19}$;

$R^{17}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

$R^{18}$, $R^{19}$ are, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

$Y^1$, $Y^2$, $Y^3$ are, independently of one another, a bond, unsubstituted or at least monosubstituted methylene, ethylene, trimethylene, tetramethylene, pentamethylene or hexamethylene, where the substituents are selected from the group consisting of: F, Cl, Br, OH, $OR^{15}$, CN, $NH_2$, $NHR^{16}$, $N(R^{16})_2$ and $C_1$-$C_{10}$-alkyl, where $R^{16}$ is selected from $C_1$-$C_{10}$-alkyl and $C_5$-$C_{10}$-aryl.

A is a bridging group. For the case that A is selected from the group unsubstituted or at least monosubstituted $C_1$-$C_6$-alkane, $C_3$-$C_{10}$-cycloalkane, $C_3$-$C_{10}$-heterocycloalkane, $C_5$-$C_{14}$-aromatic and $C_5$-$C_6$-heteroaromatic for the case (n=0), two hydrogen atoms of the bridging group are replaced by bonds to the adjacent substituents $Y^1$ and $Y^2$. For the case (n=1), three hydrogen atoms of the bridging group are replaced by three bonds to the adjacent substituents $Y^1$, $Y^2$ and $Y^3$.

For the case that A is P (phosphorus), the phosphorus forms for the case (n=0) two bonds to the adjacent substituents $Y^1$ and $Y^2$ and one bond to a substituent selected from the group consisting of $C_1$-$C_4$-alkyl and phenyl. For the case (n=1), the phosphorus forms three bonds to the adjacent substituents $Y^1$, $Y^2$ and $Y^3$.

For the case that A is N (nitrogen), the nitrogen for the case (n=0) forms two bonds to the adjacent substituents $Y^1$ and $Y^2$ and one bond to a substituent selected from the group consisting of $C_1$-$C_4$-alkyl and phenyl. For the case (n=1), the nitrogen forms three bonds to the adjacent substituents $Y^1$, $Y^2$ and $Y^3$.

For the case that A is O (oxygen), n=0. The oxygen forms two bonds to the adjacent substituents $Y^1$ and $Y^2$.

In a preferred embodiment, the process according to the invention is carried out in the presence of at least one phosphine catalyst of the general formula (V),

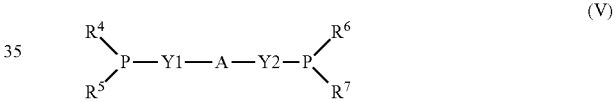

(V)

where $R^4$ to $R^7$ are, independently of one another, unsubstituted or at least monosubstituted $C_1$-$C_{10}$alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

A is i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S, where the substituents are selected from the group consisting of:

$C_1$-$C_4$-alkyl, phenyl, F, Cl, Br, OH, $OR^{16}$, $NH_2$, $NHR^{16}$ or $N(R^{16})_2$, where $R^{16}$ is selected from $C_1$-$C_{10}$-alkyl and $C_5$-$C_{10}$-aryl;

In an preferred embodiment, the process according to the invention is carried out in the presence of a phosphine catalyst of the formula I are preferred herein are those in which $R^1$, $R^2$ and $R^3$ are each phenyl or alkyl optionally carrying 1 or 2 $C_1$-$C_4$-alkyl substituents and those in which $R^1$, $R^2$ and $R^3$ are each $C_5$-$C_3$-cycloalkyl or $C_2$-$C_{10}$-alkyl. The groups $R^1$ to $R^3$ may be different or identical. Preferably the groups $R^1$ to $R^3$ are identical and are selected from the substituents mentioned herein, in particular from those indicated as preferred.

Preference is given to a trialkylphosphine as catalyst according compound (1) where $R^1$, $R^2$ and $R^3$ are alkyl groups, especially preferred is a compound (1) where $R^1$, $R^2$ and $R^3$ are the same alkyl groups.

In a preferred embodiment, the trialkylphosphine used as catalyst are tri-n-butyl-phosphine or tri-n-octyl-phosphine.

Within the context of the present invention, $C_1$-$C_{30}$-alkyl is understood as meaning branched, unbranched, saturated and unsaturated groups. Preference is given to alkyl groups having 1 to 10 carbon atoms ($C_1$-$C_{10}$-alkyl). More preference is given to alkyl groups having 4 to 8 carbon atoms ($C_4$-$C_8$-alkyl).

Examples of saturated alkyl groups are methyl, ethyl, n-propyl, isopropyl, n-butyl, isobutyl, secbutyl, tert-butyl, amyl, hexyl, n-octyl and it's isomers Examples of unsaturated alkyl groups (alkenyl, alkynyl) are vinyl, allyl, butenyl, ethynyl and propynyl.

The $C_1$-$C_{30}$-alkyl group can be unsubstituted or substituted with one or more substituents selected from the group F, Cl, Br, hydroxy (OH), $C_1$-$C_{10}$-alkoxy, $C_5$-$C_{10}$-aryloxy, $C_5$-$C_{10}$-alkylaryloxy, $C_5$-$C_{10}$-heteroaryloxy comprising at least one heteroatom selected from N, O, S, oxo, $C_3$-$C_{10}$-cycloalkyl, phenyl, $C_5$-$C_{10}$-heteroaryl comprising at least one heteroatom selected from N, O, S, $C_5$-$C_{10}$-heterocyclyl comprising at least one heteroatom selected from N, O, S, naphthyl, amino, $C_1$-$C_{10}$-alkylamino, $C_5$-$C_{10}$-arylamino, $C_5$-$C_{10}$-heteroarylamino comprising at least one heteroatom selected from N, O, S, $C_1$-$C_{10}$-dialkylamino, $C_{10}$-$C_{12}$-diarylamino, $C_{10}$-$C_{20}$-alkylarylamino, $C_1$-$C_{10}$-acyl, $C_1$-$C_{10}$-acyloxy, $NO_2$, $C_1$-$C_{10}$-carboxy, carbamoyl, carboxamide, cyano, sulfonyl, sulfonylamino, sulfinyl, sulfinylamino, thiol, $C_1$-$C_{10}$-alkylthiol, $C_5$-$C_{10}$-arylthiol or $C_1$-$C_{10}$-alkylsulfonyl.

$C_3$-$C_{10}$-cycloalkyl is understood in the present case as meaning saturated, unsaturated monocyclic and polycyclic groups. Examples of $C_3$-$C_{10}$-cycloalkyl are cyclopropyl, cyclobutyl, cyclopentyl, cyclohexyl or cycloheptyl. The cycloalkyl groups can be unsubstituted or substituted with one or more substituents as has been defined above in connection with the group $C_1$-$C_{10}$-alkyl. The reaction according to the invention uses as a catalyst at least one phosphine. In a preferred manner only one to different phosphines are used, especially preferred only one phosphine.

In a preferred way the reaction according to the invention uses as catalyst one phosphine and no metal atom or ion binding the phosphine as a ligand.

In the inventive process the amount of vinylation catalyst used based on the NH-compound can be varied in a wide range. Usually, the vinylation catalyst is used in a substoichiometric amount relative to the NH-compound. Typically, the amount of vinylation catalyst is not more than 50 mol %, frequently not more than 20 mol % and in particular not more than 10 mol % or not more than 5 mol %, based on the amount of the NH-compound. An amount of vinylation catalyst of from 0.001 to 50 mol %, frequently from 0.001 mol % to 20 mol % and in particular from 0.005 to 10 mol %, based on the amount of the NH-compound is preferably used in the process of the invention.

The reaction of a NH-compound with acetylene can principally be performed according to all processes known to a person skilled in the art which are suitable for the reaction of a NH-compound with acetylene.

The acetylene used for the vinylation reaction can be used in pure form or, if desired, also in the form of mixtures with other, preferably inert gases, such as nitrogen, argon or propan, ethan, methane. The acetylene can also be added pressureless or dissolved in an appropriate solvent as Dimethylacetamide, Dimethylformamide, NMP, Toluene, Benzene or other solvent, suitable to dissolve sufficient amount of acetylene.

The acetylene can be applied discontinuously or continuously, e.g. by bubbling acetylene gas through the reaction mixture or into the reactor or continuous feeding of acetylene into the reactor either as a reactant or dissolved in a solvent.

The reaction is typically carried at an acetylene pressure in the range from 0.1 to 20 bar, preferably in the range from 0.5 to 6 bar, more preferably in the range from 1 to 1.5 bar cold pressure.

In one embodiment of the present invention, the inventive process is characterized in that the reaction between a NH-compound and acetylene is performed at a pressure in the range from 1 to 20 bar.

The reaction can principally be performed continuously, semi-continuously or discontinuously. The vinylation reaction according to the invention is carried out in a liquid phase. This can be achieved by adding one or more solvents, preferably from the group of aliphatic as well as aromatic hydrocarbons, linear as well as cyclic ethers, linear as well as cyclic amides, sulfoxides, nitriles and halogenated hydrocarbons. Preferred solvents are toluene, DMF, Dimethylacetamide and Diglyme. The liquid phase can also be formed by the NH-compound without any additional solvent.

The reaction can principally be performed in all reactors known to a person skilled in the art for this type of reaction. Suitable reactors are described and reviewed in the relevant prior art e.g. K. Henkel, "Reactor Types and Their Industrial Applications", Ullmann's Encyclopedia of Industrial Chemistry, 2005, Wiley-VCH Verlag GmbH & Co. KGaA, chapter 3.3: "Reactors for gas-liquid reactions".

The inventive process can be performed in a wide temperature range. Preferably the reaction is performed at a temperature in the range from 20° C. to 200° C., more preferably in the range from 50° C. to 180° C., in particular in the range from 100° C. to 170° C.

EXAMPLES

Experiments in ACE-Tubes:

Inside a Glove Box (Ar), an ACE-Tube (4 mL volume, thick-walled glass tube with Teflon screwcap, sealed with a teflon O-ring) was charged with substrate (usually: Pyrrolidinone, 85.1 mg, 1.00 mmol, 1.00 equiv.) and phosphine catalyst (usually: Tributylphosphine, 20.2 mg, 0.100 mmol, 10.0 mol %). A Teflon coated magnetic stirring bar was added and the tube was filled with a freshly prepared solution of acetylene in dimethyl acetamide (DMAA) (3.50 mL, ca. 0.70 M/ca. 1.90 wt, ca. 2.45 mmol, ca. 2.45 equiv.), prepared by bubbling solvent-free and dried acetylene through absolute DMAA, or with a freshly prepared solution of acetylene in dimethyl formamide (DMF) (3.50 mL, ca. 0.60 M/ca. 1.65 wt, ca. 2.10 mmol, ca. 2.10 equiv.), prepared by bubbling solvent-free and dried acetylene through absolute DMF (concentration of substrate: 0.286 M). The tube was then sealed and heated by a metal heating block for 16 h at 120, 130 or 140° C. The tube was then cooled to room temperature and mesitylene (30.0 µL) was added as an internal GC standard. The reaction mixture was then filtered through a syringe filter and analyzed by calibrated GC or by GC in combination with ¹H-NMR.

Analysis was done on an Agilent Technologies 6890N gas chromatograph with a split/splitless injector and an FID detector. The column used was an Agilent Technologies DB-1 capillary column (30 m*0.25 mm, 1 μm) with Helium as carrier gas.

GC method: Split: 50/1, 2.0 mL/min, const. pressure, 80° C.-1 min-15° C./min-250° C.-5 min. NMR analysis was done on a Magritek Spinsolve 60 Phosphorus Ultra NMR spectrometer with an ¹H frequency of 60 MHz. The samples were measured in non-deuterated DMAA as a solvent. Proton spectra were achieved with 4 scans, 6.4 sek acquisition time per scan, 30 sek repetition time and a pulse angle of 90°. Conversion to the viny compound was detected by the three characteristic proton resonances of the vinyl group.

Characteristic example (given in ppm):

¹H-NMR (60 MHz, DMAA) δ=6.85 (dd, $^3J_{HH}$=16.2 Hz, $^3J_{HH}$=9.5 Hz, 1H, NCH), 4.10 (d, $^3J_{HH}$=16.6 Hz, 1H, NCHCH$_2$), 3.85 (d, $^3J_{HH}$=9.5 Hz, 1H, NCHCH$_2$).

Experiments in NMR-Tubes:

Inside a Glove Box (Ar), a J. Young NMR tube was charged with a solution of substrate (0.150 mmol, 1.00 equiv.) and tributylphosphine (6.1 mg, 30 μmol, 20 mol %) in absolute dimethyl acetamide (DMAA) (600 μL, 0.250 M). The tube was sealed with a septum cap and solvent-free and dried acetylene was bubbled through via steel cannula. The septum cap was then replaced inside the Glove Box with a J. Young cap. Then, the NMR tube was heated to 110° C. by a metal heating block for 1 h and subsequently analyzed by NMR spectroscopy (¹H and ³¹P). This process was repeated for 120° C., 130° C., 140° C. and once more for 140° C.

NMR analysis was done on a Magritek Spinsolve 60 Phosphorus Ultra NMR spectrometer with an ¹H frequency of 60 MHz. The samples were measured in non-deuterated DMAA as a solvent. Proton spectra were achieved with 4 scans, 6.4 sek acquisition time per scan, 30 sek repetition time and a pulse angle of 90°. Conversion to the viny compound was detected by the three characteristic proton resonances of the vinyl group.

Characteristic example (given in ppm):

¹H-NMR (60 MHz, DMAA) δ=6.85 (dd, $^3J_{HH}$=16.2 Hz, $^3J_{HH}$=9.5 Hz, 1H, NCH), 4.10 (d, $^3J_{HH}$=16.6 Hz, 1H, NCHCH$_2$), 3.85 (d, $^3J_{HH}$=9.5 Hz, 1H, NCHCH$_2$).

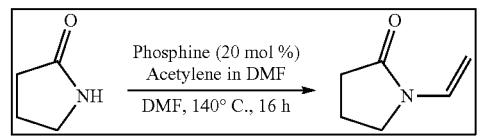

| ACE-Tube, Analysis by calibrated GC | | |
|---|---|---|
| # | Phosphine | conv./yield (sel.) |
| A | P(nBu)3 | 87%/68% (78%) |
| B | P(tBu)3 | 53%/29% (54%) |
| C | P(Cy)3 | 33%/14% (42%) |
| D | P(nOct)3 | 88%/67% (78%) |
| E | P(2-furyl)3 | trace |
| F | P(Me)3 | 72%/46% (64%) |
| G | PPh3 | 2%/1% (82%) |

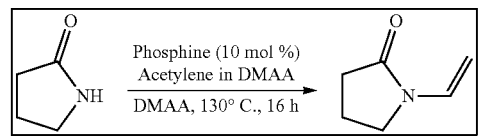

| ACE-Tube, Analysis by calibrated GC | | |
|---|---|---|
| # | Phosphine | conv./yield (sel.) |
| A | P(nBu)3 | 96%/77% (80%) |
| B | P(tBu)2Me | 97%/75% (77%) |
| C | dcpb | 100%/65% (65%) |
| D | dcpe | 83%/59% (71%) |
| E | dcpm | 91%/78% (86%) |

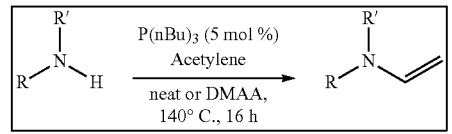

| Substrate: | $pK_a^{DMSO}$ | Yield | Conditions |
|---|---|---|---|
| ![pyrrolidinone NH] | 24.2$^a$ | isolated yield: 61% | 5 mol %, neat, 140° C., 1.5 bar C$_2$H$_2$ |
| ![pyrrolidinone NH] | 24.2$^a$ | isolated yield: 84% | 1.5 mol % P(Oct)$_3$, neat, 140° C., 6 hours, 6 bar C$_2$H$_2$ |

-continued

| Substrate: | $pK_a^{DMSO}$ | Yield | Conditions |
|---|---|---|---|
| ε-caprolactam (7-membered lactam) | 27.2[b] | isolated yield: 64% | 5 mol %, neat, 140° C., 1.5 bar $C_2H_2$ |
| isoindolin-1-one | 19.4[e] | 1H-NMR Int: 0/100 | 20 mol %, $C_2H_2$ solution in DMAA, 140° C., 1 h |
| imidazole | 18.6[c] | isolated yield: 46% | 5 mol %, DMAA, 140° C., 1.5 bar $C_2H_2$ |
| pyrrole | 23[d] | 1H-NMR Int: 15/85 | 20 mol %, $C_2H_2$ solution in DMAA, 140° C., 3 h |
| oxazolidin-2-one | 20.8[d] | 1H-NMR Int: 85/15 (GC Signals overlap) | 10 mol %, $C_2H_2$ solution in DMAA, 120° C., 16 h |
| + 5-methyl-oxazolidin-2-one | 18.4[e] | isolated yield: 52% | 5 mol %, DMAA, 140° C., 1.5 bar $C_2H_2$ |
| 5-methyl-oxazolidin-2-one | 18.4[e] | isolated yield: 53% | 4 mol % $P(Oct)_3$, neat, 140° C., 17 bar $C_2H_2$ |
| imidazolidin-2-one | 24.4[e] | GC-Int: 37 monovinyl/ 56 (Divinyl) | 5 mol %, DMAA, 140° C., 1.5 bar $C_2H_2$ |
| carbazole | 19.9[d] | isolated yield: 95% | 5 mol %, DMAA, 140° C., 1.5 bar $C_2H_2$ |
| indole | 21.0[d] | isolated yield: 83% | 5 mol %, DMAA, 140° C., 1.5 bar $C_2H_2$ |
| benzimidazole | 16.4[c] | isolated yield: 24% | 5 mol %, DMAA, 140° C., 1.5 bar $C_2H_2$ |
| 1,2,4-triazole | 14.8[c] | 1H-NMR Int: 40/60 | 20 mol %, $C_2H_2$ solution in DMAA, 160° C., 3 h |

-continued

| Substrate: | pK$_a^{DMSO}$ | Yield | Conditions |
|---|---|---|---|
|  | 19.8[c] | 1H-NMR int: 0/100 | 20 mol %, C$_2$H$_2$ solution in DMAA, 160° C., 2 h | pK$_a$-values were adapted from the literature (measured by the spectrophotometric method in DMSO against indicator at 25° C., see: J. Am. Chem. Soc. 1975, 97, 7006-7014 and J. Org. Chem. 1980, 46, 3295-3299.)
[a]F. G. Bordwell, H. E. Fried, J. Org. Chem. 1991, 56, 4218-4223.
[b]B. Valtera, M. I. Terekhova, E. S. Petrov, J. Stehlíček, J. Šebenda, Collect. Czech. Chem. Commun. 1985, 50, 834-839
[c]F. G. Bordwell, Acc. Chem. Res. 1988, 21, 456-463.
[d]F. G. Bordwell, G. E. Drucker, H. E. Fried, J. Org. Chem. 1981, 46, 632-635.
[e]pKa values calculated by DFT Not-isolated yields are usually calculated by addition of GC-resp. NMR-integrals of starting material and product and normalizing the corresponding integrals by this value. Overlapping GCsignals are integrated as automatically done by the ChemStation software, which usually leads to a slight bias towards product formation (underlying broader signal of starting material).

Experiments in Premex (Tall) Stainless Steel Autoclave:

Inside a Glove Box (Ar), a crimp vial (glass, 10 mL volume) was charged with substrate (usually: Pyrrolidinone, 170.2 mg, 2.00 mmol, 1.00 equiv.) and phosphine catalyst (usually: Tributylphosphine, 20.2 mg, 0.100 mmol) was added. If necessary, dimethyl acetamide (DMAA) was added (0.185 mL or 0.930 mL, 2.00 mmol or 10.0 mmol, 1.00 equiv. or 5.00 equiv.). %). A Teflon coated magnetic stirring bar was added and the vial was sealed with a septum cap, the septum was punctuated with a stainless steel cannula and placed inside a Premex (tall) stainless steel autoclave (60 mL volume) with a Kalrez O-ring. The autoclave was then sealed under argon, purged three times with solvent-free and dried acetylene and finally charged with acetylene (1.5 bar). The autoclave was then heated by a metal heating block for 16 h at 110-150° C. The autoclave was then cooled to room temperature and depressurized via a bubble counter. After opening the autoclave, mesitylene (30.0 µL) was added to the crimp vial as an internal GC standard and the reaction mixture was diluted with DMAA (1.5 mL). The reaction mixture was then filtered through a syringe filter and analyzed by calibrated GC or by GC in combination with $^1$H-NMR.

Analysis was done on an Agilent Technologies 6890N gas chromatograph with a split/splitless injector and an FID detector. The column used was an Agilent Technologies DB-1 capillary column (30 m*0.25 mm, 1 µm) with Helium as carrier gas.

GC method: Split: 50/1, 2.0 mL/min, const. pressure, 80° C.-1 min-15° C./min-250° C.-5 min. The measured GC signal areas, unless properly calibrated, are only supposed to be estimates due to overlapping of the starting material and the product. However, distinction between both species was clearly possible and supported by $^1$H-NMR spectroscopy.

NMR analysis was done on a Magritek Spinsolve 60 Phosphorus Ultra NMR spectrometer with an $^1$H frequency of 60 MHz. The samples were measured in non-deuterated DMAA as a solvent. Proton spectra were achieved with 4 scans, 6.4 sek acquisition time per scan, 30 sek repetition time and a pulse angle of 90°. Conversion to the viny compound was detected by the three characteristic proton resonances of the vinyl group.

Characteristic example (given in ppm):
$^1$H-NMR (60 MHz, DMAA) δ=6.85 (dd, $^3J_{HH}$=16.2 Hz, $^3J_{HH}$=9.5 Hz, 1H, NCH), 4.10 (d, $^3J_{HH}$=16.6 Hz, 1H, NCHCH$_2$), 3.85 (d, $^3J_{HH}$=9.5 Hz, 1H, NCHCH$_2$).

Autoclave Experiments:

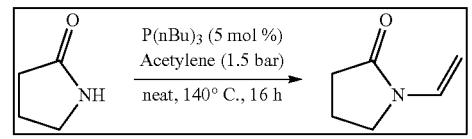

| (Premex tall 2), analysis by calibrated GC | | |
|---|---|---|
| # | temperature | conv./yield (sel.) |
| A | 110° C. | 54%/40% (74%) |
| B | 120° C. | 95%/73% (77%) |
| C | 130° C. | 94%/71% (75%) |

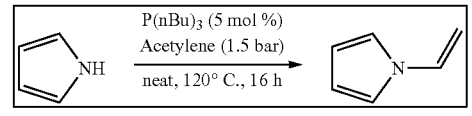

Premex tall 2, analysis by GC GC Area starting material/product: 81/19

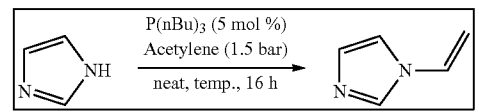

| Premex tall 2, analysis by GC | | | |
|---|---|---|---|
| # | Temp. | GC Area Imidazole | GC Area Vinylimidazole |
| A | 130° C. | 91 | 9 |
| B | 140° C. | 80 | 20 |
| D | 150° C. | 65 | 35 |

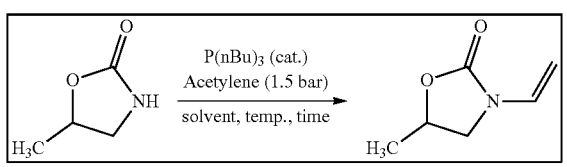

| # | catalyst | solvent | Temperature | Time | GC Area MOX | GC Area VMOX |
|---|---|---|---|---|---|---|
| A | 4 mol % | neat | 140° C. | 16 h | 77 | 23 |
| B | 4 mol % | neat | 150° C. | 16 h | 72 | 28 |
| C | 4 mol % | neat | 150° C. | 60 h | 66 | 34 |
| D | 5 mol % | DMAA (2 equiv.) | 140° C. | 16 h | 65 | 35 |
| E | 5 mol % | DMAA (10 equiv.) | 140° C. | 16 h | 45 | 55 |

Experiments in stainless steel autoclave at elevated acetylene pressure (VMOX): A 0.3-liter autoclave was charged with 100 g of 5-methyl-1,3-oxazolidin-2-one (MOX, 0.989 mol, 1 equiv.) and 16.3 g (0.0396 mol, 4 mol %) of trioctylphosphine (90%, technical grade) under inert atmosphere. The reactor was closed, filled with acetylene to 5 bar acetylene pressure, heated to 140° C. and then acetylene was passed through at 25 norm-liters/hour rate under the pressure of 17 bar for a reaction time of 16 hours. A norm-liter is one liter of a gas at 0° C. and 1013 millibar. The composition of the mixture obtained in the reactor after 16 hours of reaction was analyzed via gas chromatography and quantitative NMR.

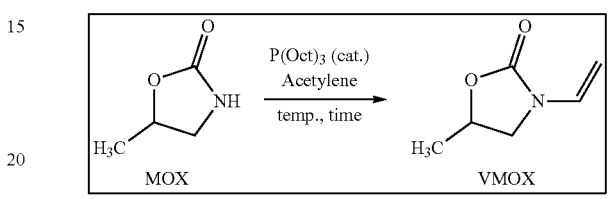

| # | Catalyst [mol %] | solvent | temperature [° C.] | Pressure [bar] | Time [h] | GC VMOX [Area %] | GC MOX [Area %] | Content VMOX/MOX [g/100 g] quantitative $^1$H-NMR |
|---|---|---|---|---|---|---|---|---|
| A | 4 | Neat | 140 | 17 | 16 | 69 | 2 | 58.3/N.A. |

Experiments in stainless steel autoclave at elevated acetylene pressure (NVP): A 0.3-liter autoclave was charged with 100 g of 2-pyrrolidinone (1.175 mol, 1 equiv.) and 7.3 g (0.018 mol, 1.5 mol %) of trioctylphosphine (90%, technical grade) under inert atmosphere. The reactor was closed, filled with nitrogen to 0.5 bar, heated to 140° C. and then filled with acetylene till 6.5 bar pressure in the reactor. The reactor pressure was kept at 6.5 bar by dosing acetylene during the course of the vinylation reaction. After the reaction was finished the reactor was cooled down to room temperature and depressurized. The composition of the mixture obtained in the reactor after 6 hours of reaction was analyzed via gas chromatography and quantitative NMR.

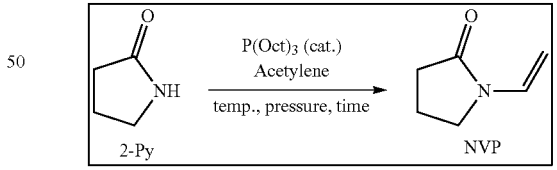

| # | Catalyst [mol %] | solvent | temperature [° C.] | Pressure [bar] | Time [h] | GC NVP [Area %] | GC 2-Py [Area %] | Content NVP/2-Py [g/100 g] quantitative $^1$H-NMR |
|---|---|---|---|---|---|---|---|---|
| A | 2 | neat | 150 | 20 | 16 | 89 | 0,6 | N.A. |
| B | 1.5 | neat | 150 | 8 | 9 | 88 | 3 | N.A. |

-continued

| # | Catalyst [mol %] | solvent | temperature [° C.] | Pressure [bar] | Time [h] | GC NVP [Area %] | GC 2-Py [Area %] | Content NVP/2-Py [g/100 g] quantitative $^1$H-NMR |
|---|---|---|---|---|---|---|---|---|
| C | 1.5 | neat | 150 | 6.5 | 6 | 85 | 3 | 84.9 ± 0.3/ 6.13 ± 0.15 |
| D | 1.5 | neat | 150 | 4.5 | 6 | 80 | 6 | 80.4 ± 0.1/ 9.41 ± 0.05 |

The invention claimed is:

1. A process for producing an N-vinyl compound by homogeneous catalysis, the process comprising:
reacting acetylene with a compound having at least one nitrogen bearing a substitutable hydrogen residue in a liquid phase in the presence of
one phosphine as a catalyst,
either a solvent selected from the group consisting of linear ethers, cyclic ethers, linear amides, cyclic amides, sulfoxides, nitriles, and halogenated hydrocarbons, or without a solvent, and
no metal atom or ion binding the phosphine as a ligand.

2. The process according to claim 1, wherein, in the compound having at least one nitrogen bearing the substitutable hydrogen residue, a $pK_a$ determined in dimethylsulfoxide of the substitutable hydrogen is in a range of 14 to 28.

3. The process according to claim 1, wherein the one phosphine used as the catalyst is a trialkylphosphine.

4. The process according to claim 3 wherein the trialkylphosphine is tri-n-butylphosphine or tri-n-octylphosphine.

5. The process according to claim 3, wherein other than the trialkylphosphine, no further catalyst is used.

6. The process according to claim 1, wherein the process is performed in the presence of a solvent selected from the group consisting of dimethyl formamide, dimethylacetamide, and diglyme, or without a solvent.

7. The process according to claim 1, wherein the produced N-vinyl-compound is at least one selected from the group consisting of 3-vinyl-5-methyl-1,3-oxazolidin-2-one and N-vinylpyrrolidinone.

* * * * *